United States Patent [19]
Salyer

[11] Patent Number: 5,980,170
[45] Date of Patent: Nov. 9, 1999

[54] TOOL DRIVER

[75] Inventor: Paul E. Salyer, Warsaw, Ind.

[73] Assignee: Othy, Inc., Warsaw, Ind.

[21] Appl. No.: 09/049,275

[22] Filed: Mar. 27, 1998

[51] Int. Cl.[6] .................................................. B23B 31/10
[52] U.S. Cl. ...................................... 408/239 R; 606/80
[58] Field of Search ............................... 606/80, 81, 180, 606/205, 206; 294/116, 100, 19.1; 408/239 R, 713, 231; 279/74

[56] References Cited

U.S. PATENT DOCUMENTS

| | | | |
|---|---|---|---|
| 3,219,376 | 11/1965 | Peters | 606/80 |
| 4,585,369 | 4/1986 | Manesse et al. | 403/322 |
| 4,887,612 | 12/1989 | Esser et al. | 128/751 |
| 5,535,754 | 7/1996 | Doherty | 128/751 |
| 5,630,818 | 5/1997 | Del Rio et al. | 606/80 |
| 5,658,290 | 8/1997 | Lechot | 606/80 |
| 5,817,096 | 10/1998 | Salyer | 606/89 |
| 5,827,316 | 10/1998 | Young et al. | 606/185 |

*Primary Examiner*—Andrea L. Pitts
*Assistant Examiner*—Adesh Bhargava
*Attorney, Agent, or Firm*—Lundy and Associates

[57] ABSTRACT

A new and improved tool driver having a shaft with a longitudinal axis and opposite ends. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool which is used with the driver has a bar which has the same dimensions as the groove in the boss of the tool driver of the invention. The bar thus fills the slot and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned.

23 Claims, 2 Drawing Sheets

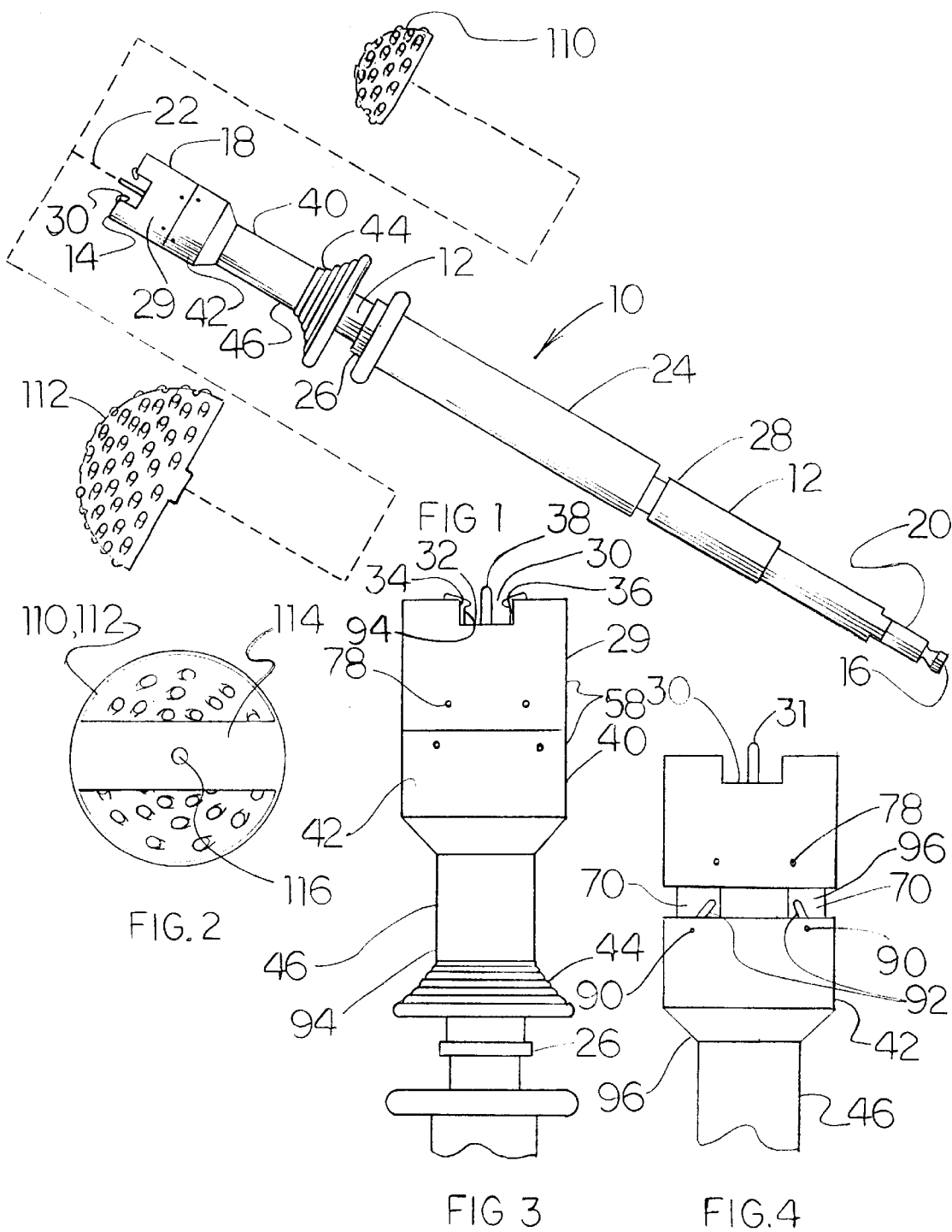

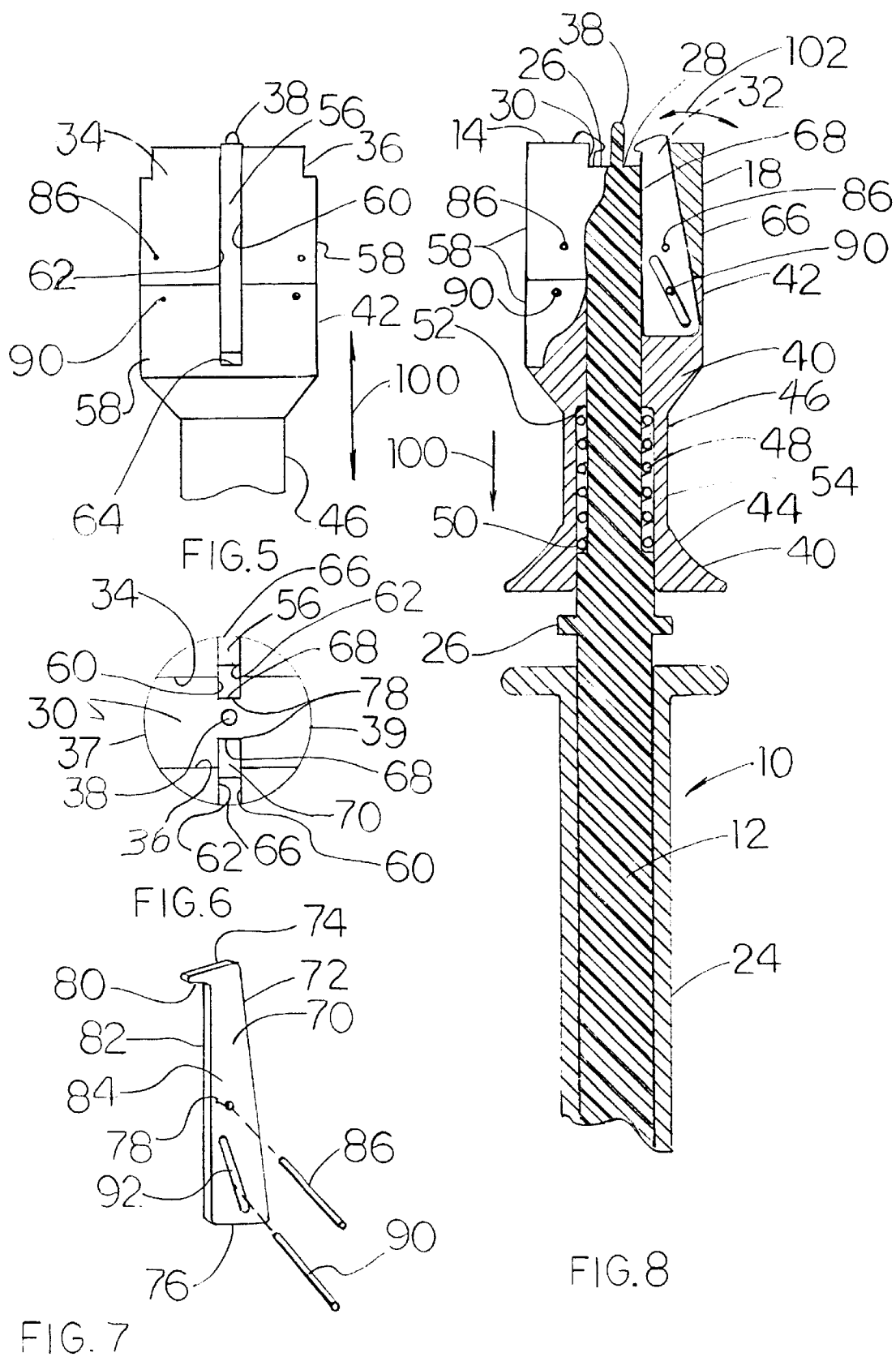

TOOL DRIVER

BACKGROUND OF THE INVENTION

The present invention pertains to tool drivers and holders for rotary tools, and more particularly a new and improved tool driver suitable for driving acetabular reamer cups and patella cutters and other surgical tools of any size which is easily cleaned and held and guided to rotate in true concentricity with the tool driver.

Patella cutters and acetabular reamer cups are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Patella cutters have a complex arrangement of precisely shaped cutting edges spirally arranged around an axis for cutting the patella. Acetabular reamer cups have a complex arrangement of cutting edges spirally arranged on a spherical surface around the axs of rotation of the cup. Both acetabular reamers and patella cutters perform better when rotated precisely around the axis around which these cutting edges are positioned by design. Additionally, precise tolerances cannot be achieved without precise axial rotation as designed.

It is therefore highly desirable to provide a new and improved tool driver. It is also highly desirable to provide a new and improved tool driver which can be used with acetabular reamer cups, patella cutters and like rotary tools. It is also highly desirable to provide a new and improved tool driver by which rotary tools may be driven about the tool driver's longitudinal axis with preciseness such that all of the cutting edges of the rotary tool function as designed.

Acetabular reamer cups also come in a full range of sizes. These sizes range from about 36 millimeters in diameter to about 72 millimeters in diameter. In the past, a specific tool driver could only be used with one or few of the sizes of available acetabular reamer cups. Thus, in any operating room there had to be several tool drivers for acetabular reamer cups. It is therefore also highly desirable to provide a new and improved tool driver by which acetabular reamer cups and patella cutters of all sizes can be driven.

Unique to some knee surgery and some hip operations is the utilization of milled bone, tissue and debris as filler to be placed between the artificial insert and the body to assist the healing process. Thus, acetabular reamer cups and patella cutters are mounted on tool drivers in a manner to collect such debris for such use. It is therefore, also highly desirable to provide a new and improved tool driver on which the rotary tools of the type which collect milled bone tissue and other debris for use as filler can be used.

In all surgery utilizing rotary tools, rotary tool holders such as used to drive rotary tools must be separable from their tool drivers to replace or sharpen as required. It may also be necessary to change tools during an operation, thus, both the rotary tools and the tool drivers must at times be cleaned, sterilized and reused. Thus, it is therefore also highly desirable to provide a new and improved tool driver which can be easily cleaned, sterilized and reused.

Some previous tool drivers grip the tool utilizing opposed pins, flanges and slots, or opposed spring loaded ball catches, or other such devices. These devices represent a problem in that the catches tend to trap dried blood and other debris which are very difficult to remove during a deaning process. It is therefore also highly desirable to provide a new and improved tool driver which is simple in construction, easy to use and does not have opposed pins, flanges, slots and other devices in which to catch debris and render the tool driver difficult to clean, sterilize and reuse.

An additional problem is that unless tolerances of tools and tool drivers are made very close, at a greatly increased cost, there is considerable free play between the tool and the tool driver. This increased play increases the wear of the cutting edges, makes more different the positioning of the tool, renders the tool useless for holding close tolerances, requires the tool not to cut as designed, and there is no possibility of utilizing the rotary tool spinning precisely about its axis as designed. It is therefore, also highly desirable to provide a new and improved tool driver which allows the rotary tool to be utilized spinning precisely about its axis, as designed.

It is also highly desirable to provide a new and improved tool driver in which close tolerances can be held.

Finally, it is highly desirable to provide a new and improved tool driver which has all of the above desired features.

SUMMARY OF THE INVENTION

It is therefore and object of the invention to provide a new and improved tool driver.

It is also an object of the invention to provide a new and improved patella driver which can be used with both acetabular cups, patella cutters and like rotary tools.

It is also an object of the invention to provide a new and improved tool driver by which rotary tools may be driven about the tool drivers longitudinal is with preciseness such that all of the cutting edges of the rotary tool function as designed.

It is also an object of the invention to provide a new and improved tool driver which acetabular reamer cups of all sizes and patella cutters can be driven.

It is also an object of the invention to provide a new and improved tool driver on which the rotary tools of the type which collect milled bone tissue and other debris for use as filler, can be used.

It is also an object of the invention to provide a new and improved tool driver which can be easily cleaned, sterilized and reused.

It is also an object of the invention to provide a new and improved tool driver which allows the rotary tool to be utilized spthunitng precisely about its axis as designed.

It is also an object of the invention to provide a new and improved tool driver which is simple in construction, easy to use and does not have opposed pins, flanges, slots and other devices in which to catch debris and render the tool driver difficult to clean, sterilize and reuse.

It is also an object of the invention to provide a new and improved tool driver in which close tolerances can be held.

It is finally an object of the invention to provide a new and improved tool driver which has all of the above desired features.

In the broader aspects of the invention, there is provided a new and improved tool driver having a shaft with a longitudinal axis and opposite ends. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool which is used with the driver has a bar which has the same dimensions as the groove in the boss of the tool driver of the invention. The bar thus fills the slot and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is an exploded side view of the new and improved tool driver of the invention showing two sizes of acetabular reamer cups and patella cutters exploded therefrom, illustrating the versatility of the new and improved tool driver of the invention;

FIG. 2 is rear view of the rotary tools illustrated in FIG. 1 showing the mounting bar of the cutter;

FIG. 3 is a fragmentary enlarged side view of the new and improved tool driver of the invention in which the latch is in its closed at rest position;

FIG. 4 is a view like FIG. 3 showing the latch of the invention in its open position;

FIG. 5 is a view like FIGS. 3 and 4 taken in a direction 900 from the direction of FIGS. 3 and 4;

FIG. 6 is a top view of the new and improved tool driver of the invention;

FIG. 7 is a perspective view of the latch member of the new and improved tool driver of the invention; and FIG. 8 is a cross-sectional view of the improved tool driver of the invention taken in the direction of FIGS. 3 and 4 showing the latch mechanism of the invention.

DESCRIPTION OF A SPECIFIC EMBODIMENT

The tool driver 10 comprises a shaft 12 having opposite ends 14, 16. At end 14, a boss 18 is secured to shaft 12. At end 16, a tool collate 20 is secured to shaft 12. Shaft 12 has an elongated axis 22 about which both boss 18 and collate 20 are positioned and rotated during use. Boss 18, collate 20 and shaft 22 are coaxial and aligned in an end to end relation. Coaxially positioned on the shaft 12 is a handle 24. Handle 24 is free to rotate around the shaft 12. The handle 24 is positioned between a pair of spaced apart rings 26, 28 which are secured to the shaft 12.

Boss 18 has an exterior distal surface 29 and a groove 30 cut therein which extend transversally of the shaft 12 across end 14 between diametrically opposite portions of boss 18. Groove 30 has a bottom 32 and upstanding sides 34 and 36. A centering pin 38 is secured to shaft 12 and extends coaxially thereof outwardly of bottom 32. In the specific embodiment illustrated, pin 38 is equidistant between groove walls 34, 36 and equally positioned between opposite groove ends 37, 39 and extends coaxially beyond end 14.

Positioned on shaft 12 between the boss 18 and ring 26 is a latch actuator 40. Latch actuator 40 is slideable axially along shaft 12 and, in the specific embodiment illustrated, is generally coaxial of the shaft 12. Latch actuator 40 has a boss end 42 and a thumb trigger 44 spaced apart by a mediate portion 46 which are formed integrally as a single piece. Latch actuator 40 is resiliently urged against boss 18 as shown in FIGS. 5 and 8 by a spring 48 which is coaxially positioned on shaft 12 between step 50 on shaft 12 and actuator 40.

Boss end 42 also has an exterior surface 29 which when boss end 42 is urged against boss 18 is a continuation of exterior of surface 29 of boss 18. Spring 48 is compressed between an annular step 50 in shaft 12 and the bottom 52 of an annular groove 54 cut into mediate portion 46 between boss portion 40 and thumb trigger 44 of actuator 40 as shown in FIG. 8.

Both boss 18 and boss end 42 of actuator 44 have latch slots 56 formed therein which extend from the exterior surface 29 of boss 18 and boss end 42 inwardly. Latch slots 56 each have opposite sides 60, 62, a bottom 64, an open side 66, and a closed side 68. Positioned within these latch slots are latch pieces 70 such as illustrated in FIG. 7.

Each latch piece 70 has an elongated body 72 having opposite ends 74, 76, a medial pivot bushing 78 and a hook portion 80. Latch pieces 70 are made from sheet stock and cut to have opposite ends 74, 76, and opposite sides 82, 84. Pin 86 extends through a bushing 78 and into boss portion 18 when latch pieces are positioned within slots 56. A follower 90 is extended through an angular slot 92 and secured to boss end 42 of actuator 40.

Referring to FIGS. 6 and 8, latch members 70 are shown in their "at rest" position in which hook portions 80 extend into groove 30 adjacent to pin 38. Hook portions 80 are moveable between their "at rest" position 94 shown in FIGS. 3, 6 and 8 and their retracted position 96 shown in FIG. 4. Actuator 40 is slideable axially of shaft 12 as indicated by the arrow 100 against the resiliency of the spring 48 into its retracted position 96 shown in FIG. 4. When moving actuator 40 away from boss 18, follower 90 moves in slot 92 which pivots latch member 70 about pivot 78 as indicated by arrow 102 from their "at rest" position 94 to their retracted position 96 the latch members completely within boss portion 18 but not within groove 30 as shown in FIG. 4.

The rotary tools useful with the tool driver of the invention may include a variety of different types. Both acetabular reamer cups 110 and patella cutters 112 of various sizes ranging from 36 millimeters in diameter to 72 millimeters in diameter may be utilized. Each of these rotary tools have a mounting bar 114 secured to the tool. The mounting bar 114 has dimensions complementary of groove 30 and a hole 116 coaxial of the tool holder 10 and dimensions complementary of pin 38.

In a specific embodiment, shaft 12, actuator 46, and rotary tool such as the acetabular reamer cups 110 and patella cutters 112 are each made of stainless steel. The shaft has a diameter from about 0.0485 inch to about 0.505 inch, the actuator 40 has a diameter from about 1.125 inches to about 1.135 inches, shaft 12 has an axial length from about 7 inches to about 7.125 inches, actuator 40 has an axial length from about 2 inches to about 2.0625 inches, slot groove 30 has a width from about 0.495 inch to about 0.505 inch, and a length from about 1.129 inches to about 1.130 inches. Slots 56 have an axial length from about 1.215 inches to about 1.225 inches, a width from about 0.125 inch to about 0.135 inch, and a thickness from about 0.410 inch to about 0.420 inch. Latch pieces 70 have a length from about 1.250 inches to about 1.900 inches, a width from about 0.120 inch to about 0.125 inch, and a thickness from about 0.200 inch to about 0.220 inch. Bushing 86 is about 0.062 inch to about 0.070 inch from end 74 and from about 0.062 inch to about 0.070 inch from side 82. Angular slot 92 is about 0.062 inch to about 0.065 inch in thickness and is from about 0.850 inch to about 0.860 inch from end 76 and angles from about 17 inches to about 17.5 inches from sides 82 and 84. Mounting bar 114 has a thickness from about 0.120 inch to about 0.130 inch, and a width from about 0.490 inch to about 0.495 inch. Its length is dependent upon the diameter of the rotary tool. Hole 116 is positioned at its center an equal distance between its opposite ends and sides and has a diameter of about 0.125 inch. Pin 38 has a diameter from about 0.124 inch to about 0.125 inch.

In operation, the improved tool driver 10 of the invention can be utilized to tightly grip and easily receive rotary tools such as acetabular reamer cup 110 and patella cutters 112 of a variety of sizes. The rotary tools each have an open end across which is secured mounting bar 114. The rotary tool of choice may be secured to tool driver 10 by grasping the tool driver 10 by the handle 24. In this position handle 24 is held between the fingers and the palm of a hand and the thumb can be positioned on the trigger 44. From this position, the thumb can move the actuator 40 against the urging of the spring 48 axially towards the handle 24. This movement of the actuator 40 from its at rest position 94 pivots the latch pieces 70 out of the groove 30 allowing the mounting bar 114 of the rotary tool to be positioned in the groove 30. Releasing the trigger 44 and allowing the spring 48 to move the actuator 40 in the opposite axial direction against the boss portion 18 of the shaft 12 pivots the latch pieces 70 so as to position to hook portions 80 within the groove 30 and to hold mounting bar 114 in groove 30 and the rotary tool onto end 14 of shaft 12.

Specifically, the actual movement of the actuator 40 towards the handle 24, causes the followers 90 to move within the latch slots 56 within the latch pieces 70. The movement of the follower 90 in the latch slots 56 generally in a direction towards the handle 24 causes the latch pieces to pivot about the pivot pin 78 and to move the hook portions 80 radially outwardly of the shaft 12 and to remove them from the groove 30. The movement of the latch pieces 70 is all within the latch slots 56, within the boss 18 and within the boss portion 42 of actuator 40. Thus, no portion of the latch piece 70 protrudes from the boss 18 of the shaft 12 or the boss portion 42 of the actuator 40.

Similarly, the movement of the actuator 40 away from the handle 12 toward end 14 of the shaft 12 by the spring 48 moves the follower 90 within the latch slots 56 of the latch pieces 70 generally axially away from the handle 24. This movement of the follower 90 pivots the latch pieces 70 about the pivot pin 78 to move the hook portions thereof radially inwardly and to position the hook portions within groove 30.

The cross-sectional dimensions of the groove 30 taken through the hook portions of the latch piece 70 are complementary to the cross-sectional dimensions of the mounting bar 114 of each of the rotary tools used with the tool driver 10 of the invention.

In a specific embodiment, this cross-section measures from about 0.250 inch about 0.270 inch plus or minus 0.500 inch by 0.505 inch plus or minus 0.005 inch of the groove 30. Similarly, the mounting bar cross-section is dimensioned as 0.500 inch plus or minus 0.005 inch by 0.200 inch plus or minus 0.005 inch. Thus exactly fitting mounting bar 114 in groove 30 with tolerances of plus or minus 0.005 inch.

Similarly, mounting bar hole 116 and pin 38 have a diameter which are complementary to each other. In a specific embodiment, pin has a diameter of 0.125 inch plus or minus 0.001 inch and hole 116 has a diameter of 0.128 inch plus or minus 0.001 inch.

Therefore each rotary tool used with the improved tool driver 10 is exactly coaxially positioned on shaft 12 within the tolerances of plus or minus 0.005 inch.

The improved tool driver 10 of the invention provides a new and improved tool driver which can be used with both acetabular reamer cups and patella cutters and other like rotary tools. By the improved tool driver of the invention these rotary tools may be driven about the longitudinal axis of shaft 12 with precision such that all of the cutting edges of the rotary tool will function as designed. Additionally, the improved tool driver of the invention can be used with rotary tools of all sizes, those which collect milled bone tissue and other debris for use as filler, those which do not. The new and improved tool driver invention can be easily cleaned, sterilized and reused as well as the rotary tools with which it is used.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove axially of said boss.

2. The tool driver of claim 1 wherein said pin extends coaxially outwardly of said shaft and said boss.

3. The tool driver of claim 1 wherein said boss is coaxially of said shaft and formed together with said shaft as one piece.

4. The tool driver of claim 1 wherein said rotary tool has an axis about which said tool is rotated during use, a mounting bar extending transversely of said axis, a hole in said mounting bar coaxially of said axis, said hole being complementary of said pin.

5. The tool driver of claim 3 wherein said mounting bar is complementary of said groove.

6. The tool driver of claim 1 wherein said rotary tool is smaller in diameter than said boss.

7. The tool driver of claim 1 wherein said tool diameter is larger in diameter than said boss.

8. The tool driver of claim 1 wherein said latch mechanism further comprises a pair of diametrically opposed latch slots in said boss, and a latch piece positioned within each of said latch slots and pivotally connected to said boss, said latch pieces being moveable from a latch position in which said latch pieces hold said mounting bar within said groove to a release position in which said mounting bar can be removed from said groove.

9. The tool driver of claim 1 wherein said groove has a bottom, said bottom facing outwardly of said distal end, and a pair of oppositely facing upstanding sides.

10. The tool driver of claim 9 wherein said mounting bar has a surface having a width equal to the width of said bottom.

11. The tool driver of claim 9 wherein said mounting bar has side surfaces having a height substantially equal to said upstanding groove sides.

12. The tool driver of claim 9 wherein said groove bottom and groove sides are surface to surface with said mounting bar bottom and sides, respectively when said rotary tool is positioned on said boss.

13. The tool driver of claim 8 wherein said latch pieces are biased toward said latch position.

14. The tool driver of claim 8 further comprising an actuator, said actuator being slideably positioned on said shaft, a spring being positioned between said actuator and shaft biasing said actuator toward said boss and said latch pieces into said latch position.

15. The tool driver of claim 14 wherein said actuator has a pair of oppositely disposed latch slots therein forming a continuation of said boss latch slots, said latch pieces being within said latch slots, said latch pieces having a slot therein, said actuator having a follower in said slot, said follower moving within said slot when said actuator is moved between said latch position, and said release position, said movement of said follower in said latch piece slots pivoting said latch pieces from said latch position to said release position of said latch pieces as said actuator moves away from said boss.

16. The tool driver of claim 14 further comprising a handle on said shaft, said handle being spaced from said boss by said actuator, said handle being rotatable about said axis independently of said shaft.

17. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said rotary tool has an axis about which said tool is rotated during use, a mounting bar extending transversely of said axis, a hole in said mounting bar coaxially of said axis, said hole being complementary of said pin.

18. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said rotary tool has an axis about which said tool is rotated during use, a mounting bar extending transversely of said axis, a hole in said mounting bar coaxially of said axis, said hole being complementary of said pin, wherein aid mounting bar is complementary of said groove.

19. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said rotary tool has an axis about which said tool is rotated during use, a mounting bar extending transversely of said axis, a hole in said mounting bar coaxially of said axis, said hole being complementary of said pin, wherein said mounting bar is complementary of said groove, wherein said latch mechanism further comprises a pair of diametrically opposed latch slots in said boss, and a latch piece positioned within each of said latch slots and pivotally connected to said boss, said latch pieces being moveable from a latch position in which said latch pieces hold said mounting bar within said groove to a release position in which said mounting bar can be removed from said groove.

20. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said rotary tool has an axis about which said tool is rotated during use, a mounting bar extending transversely of said axis, a hole in said mounting bar coaxially of said axis, said hole being complementary of said pin, wherein said mounting bar is complementary of said groove, wherein said latch mechanism further comprises a pair of diametrically opposed latch slots in said boss, and a latch piece positioned within each of said latch slots and pivotally connected to said boss, said latch pieces being moveable from a latch position in which said latch pieces hold said mounting bar within said groove to a release position in which said mounting bar can be removed from said groove, wherein said groove has a bottom, said bottom facing outwardly of said distal end, and a pair of oppositely facing upstanding sides, wherein said mounting bar has a surface having a width equal to the width of said bottom, said groove bottom and groove sides are surface to surface with said mounting bar bottom and sides, respectively when said rotary tool is positioned on said boss.

21. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said latch mechanism further comprises a pair of diametrically opposed latch slots in said boss, and a latch piece positioned within each of said latch slots and pivotally connected to said boss, said latch pieces being moveable from a latch position in which said latch pieces hold said mounting bar within said groove to a release position in which said mounting bar can be removed from said groove, wherein said groove has a bottom, said bottom facing outwardly of said distal end, and a pair of oppositely facing upstanding sides, wherein said mounting bar has a surface having a width equal to the width of said bottom, wherein said groove bottom and groove sides are surface to surface with said mounting bar bottom and sides, respectively when said rotary tool is positioned on said boss.

22. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said rotary tool has an axis about which said tool is rotated during use, a mounting bar extending transversely of said axis, a hole in said mounting bar coaxially of said axis, said hole being complementary of said pin, coaxially of said axis, said hole being complementary of said pin, wherein said mounting bar is complementary of said groove, wherein said latch mechanism further comprises a pair of diametrically opposed latch slots in said boss, and a latch piece positioned within each of said latch slots and pivotally connected to said boss, said latch pieces being moveable from a latch position in which said latch pieces hold said mounting bar within said groove to a release position in which said mounting bar can be removed from said groove, wherein said latch pieces are biased toward said latch position.

23. A tool driver comprising a shaft having opposite ends and a longitudinal axis, a boss secured to said shaft at one of said ends by which said tool driver is connected to a rotary tool, a tool collet secured to said shaft at the other of said ends by which said tool driver is connected to the chuck of a surgical hand piece, said boss having a distal end surface and a groove in said distal end surface both extending transversely of said axis, a pin in said groove extending coaxially of said shaft and said boss, and a latch mechanism for holding the mounting bar of a rotary tool impaled on said pin in said groove, whereby rotary tools of all sizes can be removeably secured to said tool driver coaxially of said shaft within said groove, wherein said rotary tool has an axis about which said tool is rotated during use, a mounting bar extending transversely of said axis, a hole in said mounting bar coaxially of said axis, said hole being complementary of said pin, wherein said mounting bar is complementary of said groove, wherein said latch mechanism further comprises a pair of diametrically opposed latch slots in said boss, and a latch piece positioned within each of said latch slots and pivotally connected to said boss, said latch pieces being moveable from a latch position in which said latch pieces hold said mounting bar within said groove to a release position in which said mounting bar can be removed from said groove, wherein said latch pieces are biased toward said latch position, wherein said actuator has a pair of oppositely disposed latch slots therein forming a continuation of said boss latch slots, said latch pieces being within said latch slots, said latch pieces having a slot therein, said actuator having a follower in said slot, said follower moving within said slot when said actuator is moved between said latch position, and said release position, said movement of said follower in said latch piece slots pivoting said latch pieces from said latch position to said release position of said latch pieces as said actuator moves away from said boss.

\* \* \* \* \*